United States Patent [19]

Hansen et al.

[11] Patent Number: 5,293,770
[45] Date of Patent: Mar. 15, 1994

[54] CALIBRATION DEVICE FOR USE IN CALIBRATING A SENSOR

[75] Inventors: Steffen T. Hansen, Copenhagen; Poul R. Sorensen, Lyngby, both of Denmark

[73] Assignee: Radiometer A/S, Copenhagen, Denmark

[21] Appl. No.: 634,111
[22] PCT Filed: Apr. 20, 1989
[86] PCT No.: PCT/DK89/00092
§ 371 Date: Dec. 21, 1990
§ 102(e) Date: Dec. 21, 1990
[87] PCT Pub. No.: WO90/01160
PCT Pub. Date: Feb. 8, 1990

[30] Foreign Application Priority Data

Jul. 21, 1988 [DK] Denmark .................. 4083/88

[51] Int. Cl.⁵ .................................. G01N 27/26
[52] U.S. Cl. .................................. 73/1 R; 73/1 G; 204/401; 436/8
[58] Field of Search ............ 73/1 R, 1 G; 204/401; 436/8

[56] References Cited

U.S. PATENT DOCUMENTS

| | | | |
|---|---|---|---|
| 2,853,873 | 9/1958 | Hollobaugh et al. | 73/1 G |
| 3,061,920 | 11/1962 | Johnson | 73/1 R |
| 3,817,108 | 6/1974 | Principe et al. | 73/1 G |
| 4,172,378 | 10/1979 | Limp | 73/1 G |
| 4,635,467 | 1/1987 | Hoffa et al. | 73/1 G |
| 4,643,976 | 2/1987 | Hoskins | 436/8 |
| 4,663,958 | 5/1987 | Matthiessen | 73/1 G |
| 4,689,308 | 8/1987 | Gerhard | 436/8 |
| 4,700,560 | 10/1987 | Hoffa et al. | 73/1 G |
| 4,742,708 | 5/1988 | Porter | 73/1 G |
| 4,900,422 | 2/1990 | Bryan et al. | 204/401 |
| 4,998,431 | 3/1991 | Jappinen et al. | 73/1 G |
| 5,086,642 | 2/1992 | Jessel et al. | 73/1 G |

OTHER PUBLICATIONS

Leaflet relating to the TCM3-Monitor.
Copies of pp. 1.1-1.5 from a User's Handbook describing the TCM3.

*Primary Examiner*—Hezron E. Williams
*Assistant Examiner*—George M. Dombroske
*Attorney, Agent, or Firm*—Bryan Cave; David M. Klein

[57] ABSTRACT

In one embodiment the calibration device (1) comprises a housing (2) which by means of a removable lid (8) and a rupturable barrier layer (3) is divided into a calibration chamber (4) and a second chamber (10). The calibration chamber (4) contains a calibration fluid (5)—e.g. a dry gas—while second chamber (10) contains a second fluid (11)—e.g. a wetting agent. Immediately prior to a calibration process the lid (8) is removed, whereafter a sensor with its measuring surface in front is inserted through the second chamber (10) into the housing (2) until it abuts against a shoulder (6) in the housing (2). This causes the barrier layer (3) to rupture and the second fluid (11) to contact the calibration fluid (5). Hereafter the calibration process can take place. In another embodiment the device (1) further comprises a membrane (12) which is accommodated in the second chamber (10) and is adapted to be secured to the sensor during the insertion of the sensor into the housing (2). The disclosed device—which is particularly suited for use in calibrating sensors for transcutaneous registering of the contents of $CO_2$ and/or $O_2$ in blood—is self-contained, and can be made in a very compact design, making it very well suited for use in connection with portable equipment. The device is also suitable for being manufactured in the form of a disposable unit.

29 Claims, 5 Drawing Sheets

CALIBRATION DEVICE FOR USE IN CALIBRATING A SENSOR

This invention relates to a calibration device for use in calibrating a sensor, and of the type comprising a calibration housing with a calibration chamber, said calibration chamber containing a fluid for use in the calibration process and further including a wall part adapted to cooperate with the sensor in such a way that during the calibration process the requisite contact for this purpose is established between the sensor and the fluid contained in the calibration chamber.

Sensors are utilized in a wide range of applications in which more or less frequently a measurement of the content of one or more components in a given fluid is desired, or where it is desired to establish a measurement of the condition of such a fluid e.g. as expressed by the pH-value of the fluid.

The components in question may exist in a gaseous state or in a non-gaseous state and may be present in either a liquid or in a gas.

The following components may be stated as examples of non-gaseous components the content of which it is often desired to register: Ions (such as $H^+$, $K^+$, $Na^+$, $Ca^{2+}$, $Cu^{2+}$, $Cl^-$ etc.) and organic molecules (e.g. glucose, metabolites, hormones, enzymes etc.). Examples of gaseous components include various gases such as $O_2$, $NH_3$ and $CO_2$. Such gases are typically registered in the form of their respective partial gas pressures ($pO_2$, $pNH_3$ and $pCO_2$). Examples of fluids in which the above components may be present are various physiological liquids (e.g blood), various types of water (e.g. fresh water, seawater, sewage water etc.) nutritive mediums, laboratory samples of all sorts, flue gases, air etc.

As to typical sensors these include sensors based on various electro-chemical measuring principles such as potentiometry, amperometry and polarography as well as optical sensors, i.e. sensors utilizing an optical response phenomenon.

Common to the majority of these sensors is the fact that prior to a measuring sequence the sensor with accompanying equipment must be calibrated.

Such a calibration typically involves contacting the sensor with a fluid having a known content of the component to which the sensor is sensitive.

Thus, in performing the calibration process it is necessary to have access to a calibration fluid of a known composition. Also it is advantageous if the calibration fluid is available in a form in which the requisite contact with the sensor is readily obtained.

Even though it is sometimes necessary or preferred to prepare the actual calibration fluid immediately before the calibration process, it is normally preferred to make use of a prefabricated calibration fluid. In case of such a prefabricated calibration fluid it goes without saying that it is of vital importance to store said fluid under such conditions that the original composition does not change with time e.g. as a result of mixing or reaction with other materials or the surroundings.

In this connection it is noted that handling of calibration fluids intended for use in calibrating gas sensors, in particular sensors for $pO_2$ and $pCO_2$, poses special problems due to the fact that the contained components tend to interact with the surroundings. Consequently it is necessary, both during storage and use of such fluids, to take special precautions in order to minimize or eliminate the risk of any such unwanted interaction. The optimum solution to this problem is of course to store the fluid in question in a sealed chamber until the time of use. In connection with the calibration process proper the best solution is to ensure that the contact between the sensor and the calibration fluid be established in a way which positively excludes any prior contact between the calibration fluid and the surroundings.

Another demand which has become topical concurrent with the development of portable measuring equipment is, that the auxiliary equipment used in connection with the portable measuring equipment proper, must not in itself—due to its size, shape or weight—reduce the portability of the total equipment or complicate the use of same.

Since the calibration equipment is a central part of the total measuring equipment it goes without saying that said calibration equipment should also, to the maximum extent possible, comply with the above mentioned demand.

Present commercially available calibration equipment does not to any significant degree possess the quite considerable degree of portability possessed by recent, very compact measuring units.

One such very compact measuring unit is the TCM3-monitor for transcutaneous measuring of the $O_2$ and/or the $CO_2$ content in blood, said unit being developed and marketed by the Danish company RADIOMETER A/S. Having external dimensions of ca. 24×8×23 cm and having a weight of 2.7 kg this unit is truly portable. This portability is, however, considerably impaired by the fact that during calibration the unit demands usage of a separate, relatively bulky calibration device.

Said calibration device—which by and large consists of a bottle containing pressurized calibration gas ($O_2$ and/or $CO_2$)—is to be connected via a flexible hose to a calibration house on the monitor, the calibration house also being adapted to accommodate the sensor. The calibration device is not designed for permanent securing to the monitor and the two units thus cannot be handled as one self-contained unit. In all circumstances such a combined unit would possess a considerably lower degree of portability as compared to the TCM3-monitor proper, due to the size and weight of the calibration device (ca. 12×8×23 cm, 1.9 kg).

U.S. Pat. No. 4,635,467 (Hoffa et al.) discloses a calibration device as described in the opening portion of the present description. Said device comprises a liquid filled tube which in either or both ends is delimited by means of a fluid-tight, gas permeable membrane. A further membrane, also being fluid and permeable to gas, forms a wall part which is adapted to abut the measuring surface of the sensor during calibration. Until the time of use all three membranes are covered by separate, manually detachable lids.

In calibrating for gaseous components it is necessary to have access to an external source of calibration gas. This source—which necessarily will be in the form of a separate unit—is to be connected to the gas inlet of the device upon removal of the lids of the device and securing of the latter to the sensor. Upon a completed calibration process the gas source is to be disconnected from the de3: vice.

Thus, the calibration device according to U.S. Pat. No. 4,635,467 is not convenient in use. Also the need for a separate gas source entails that the device be less suited for use in connection with portable equipment.

Accordingly there exists a need for a compact calibration equipment which is well suited for use in connection with portable measuring equipment, which is convenient to handle and which does not call for special precautions in connection with storage or use and which further provides for the possibility of establishing optimum conditions during calibration.

The above referred need is met by the calibration device according to this invention, said device being characteristic in that the calibration chamber consists in a closed, fluid-tight chamber, that said wall part consists in a fluid-tight, rupturable and preferably non-elastic barrier layer, which is adapted to be ruptured by contact with the sensor, and in that the fluid in the calibration chamber is a calibration fluid containing all the components necessary for the calibration process.

Such a calibration device can be designed very simply thus making it particularly suited for mass production in the form of a disposable unit, thereby achieving various efficiency related advantages. The physical shape of the calibration device depends alone on the shape of the sensor with which it is to be used and the device can be used in connection with calibration of sensors for registering both gaseous and non-gaseous components.

Besides, such a disposable device or unit allows for the possibility of maintaining the sensor in a calibrated, ready-to-use state for extended periods of time, without continuously consuming calibration fluid.

A further advantage of such a disposable calibration device is that it may be utilized as a quality control device when filled with a fluid of predetermined composition. A quality control device is used to determine or test the reliability of measuring equipment. In this connection it is to be understood that the calibration device according to this invention is not in any way limited to the above-mentioned two areas of application but is applicable within a wide range of applications where the task is to contact a sensor with a predetermined fluid.

The fact that the calibration chamber is delimited by a rupturable barrier layer provides for a considerable degree of user-friendliness in that the requisite contact between the calibration fluid and the sensor is obtained simply by forcing the sensor through the barrier layer.

Further the above mentioned risk of "pollution" of the calibration fluid—this risk being particularly distinct in connection with a gaseous calibration fluid—is prevented in that the calibration fluid is prevented from interacting with the surroundings before or during the calibration process. On completed calibration the sensor and the calibration device are separated and the latter may be discarded.

In principle, a calibration process demands that only the components relevant to the calibration be present in the calibration chamber. Yet, it is sometimes desirable to be able to supply a supplementary fluid to the calibration chamber in order to make the calibration "atmosphere" contacting the sensor simulate the actual conditions on the measuring site in question.

If, for example, the task is to register the presence of a gaseous component, e.g. $O_2$, in a liquid, it is, with a view to optimizing the accuracy of the measurement, advantageous to perform a so-called "wet" calibration process, i.e. a calibration utilizing a "wet" calibration gas. This could simply be effected by using a wet calibration gas in the calibration chamber. Such an approach will, however, often entail problems in the form of inaccurate calibrations and thus erroneous measurements, due to the risk of unintended interaction between the chemically quite reactive $O_2$ and possible impurities or other foreign components present in the calibration chamber. Any such interaction would mean that the $O_2$-value would slowly drift away from its basic, predetermined value.

Thus, in case a wet calibration is to be performed it is advantageous to store the calibration gas in a "dry" state and not wet it until the calibration process actually takes place.

Consequently a preferred embodiment of the disclosed calibration device is characterized in that the housing comprises a second chamber, said second chamber being delimited by the housing, the side of the barrier layer facing away from the calibration chamber and a lid extending by and large parallel to the barrier layer, and in that the second chamber contains a second fluid which contacts the calibration fluid of the calibration chamber upon rupture of the barrier layer.

This provides in a simple manner for a positive separation of the calibration fluid and the wetting agent. The wetting automatically occurs when the sensor ruptures the barrier layer due to the thus established connection between the second chamber and the calibration chamber. The lid which together with the housing delimits the second chamber is advantageously manually removable, but may also take the form of a rupturable lid which is to be ruptured by the sensor, similar to the barrier layer.

Some of the various types of sensors, in particular gas sensors, use a semi-permeable membrane allowing passage of—and thus registering of—the actual components while excluding other components.

Depending on the type of membrane and the use of same, the membrane has to be replaced at regular intervals. The optimum interval for replacement would be in connection with each new measuring cycle i.e. in connection with each calibration. In practice, however, such a frequent replacement will rarely take place i.a. due to the fact that the membrane replacement procedure—depending on the technique used—may be of a more or less complicated nature and/or time consuming. In some cases where the replacement procedure is carried out by means of easy operable, discardable devices, the reason for less frequent replacements of the membrane may be found in the cost of such discardable devices.

In the light of the above discussed circumstances, a further embodiment of the calibration device according to the invention is characteristic in that a membrane, which is permeable to the components relevant to the calibration process, is arranged on the side of the barrier layer facing away from the calibration chamber, said membrane extending by and large parallel to the barrier layer, and in that the device comprises fixing means being adapted to cooperate with the membrane and the sensor in such a way that the membrane is secured to the sensor in a stretched out state upon moving the sensor and the membrane against each other in a direction by and large perpendicular to the plane of the membrane.

By adding to the calibration device according to the invention such an integral membrane it is in a simple manner made possible to replace the membrane and calibrate the sensor in one single procedure. This provides for a considerably increased degree of user-friendliness.

The membrane proper may consist of a polymeric membrane, known per se, which on the side facing the sensor has fastening or fixing means in the form of a ring having an annular projection adapted to engage a complementary recess on the sensor. Alternatively the securing of the membrane to the sensor may be effected by means of a separate, resiliently deformable fixing ring in the form of an "O-ring" or the like, situated on the side of the membrane facing away from the sensor. Upon pressing the calibration device against the sensor said ring will "roll" the membrane onto the sensor and from the "outside" keep the membrane attached to the sensor.

Said principle—incidentally known from prior art application devices of the discardable type—possesses in comparison with sensors using an electrolyte between the membrane and the measuring surface of the sensor the advantage of a very high degree of certainty that no air bubbles be trapped in the electrolyte, this being of importance to the measuring accuracy.

In connection with the latter fastening principle it may be necessary with some sort of guiding surface to assist the application of the fixing ring. This surface may form a part of an abutment surface integral with the housing, said abutment surface determining the distance to which the sensor is able to extend into the housing, but may also take the form of a separate guiding surface.

The invention will now be explained in detail with reference to the accompanying drawing in which.

Figure 1:
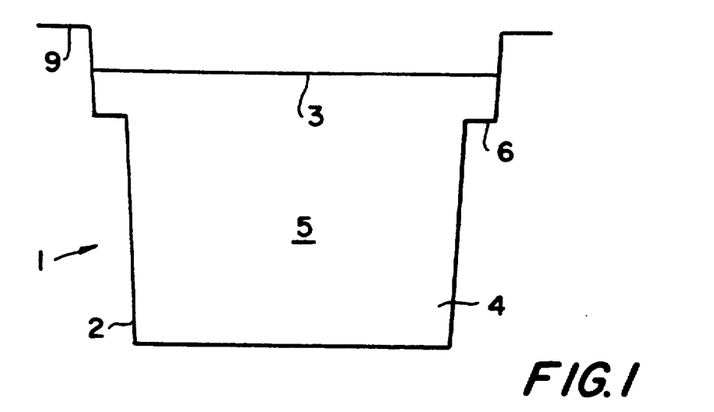
FIG. 1 shows a section through a first embodiment of a calibration device according to the invention, FIG. 2 a section through a second embodiment of the calibration device according to the invention, FIG. 3 a section through a third embodiment of the calibration device according to the invention, FIG. 4 a view illustrating the calibration device of FIG. 3 at the beginning of a combined membrane replacement and sensor calibration procedure, FIG. 5 a view, on a larger scale, of a part of the membrane ring, seen "from below", FIG. 6 a partial section, on a larger scale, of the calibration device of FIG. 4 after the membrane replacement procedure, and during a calibration process, FIG. 7 a partial section, on a larger scale, through a fourth embodiment of the calibration device according to the invention and with an alternative membrane arrangement, FIG. 8 a partial section, on a larger scale, through a fifth embodiment of the calibration device according to the invention, FIG. 9 a perspective view, on a larger scale, of another embodiment of a membrane ring, FIG. 10 a partial section, on a larger scale, through a calibration device incorporating the membrane ring of FIG. 9 and depicting the elements just prior to a combined calibration and membrane replacement procedure, and FIG. 11 a partial section similar to the one shown in FIG. 9, but depicting the elements during such a procedure.

The calibration device appearing in FIG. 1 consists of a calibration housing 2, in which is accommodate a barrier layer 3. Barrier layer 3 together with housing 2 defines a closed calibration chamber 4 in which the actual calibration fluid 5 is placed. The housing is of by and large circular cylindrical shape and is made of a material which is impermeable to the actual fluid 5, which does not interact with this fluid and which at the same time gives the housing the necessary strength. Suitable materials for the housing includes various metals such as aluminum, copper, brass etc. but also glass and various types of plastics could be used. In the latter case, it might, however, prove necessary—with a view to the tightness of the housing—to provide the housing with an interior coating of a metallic material e.g. applied electrochemically. The housing proper may be manufactured by any convenient method e.g. by casting, machining or deep-drawing. At present it is preferred to manufacture the housing by deep-drawing of an aluminum foil having a thickness of about 0.15 mm.

The barrier layer also has to be tight against the actual fluid and is preferably made from an aluminum foil of a thickness about 0.02–0.04 mm.

Both aluminum foils used may have a coating of a thin polymeric foil on at least the one side, this making it possible to bond the barrier layer to the housing in a simple manner by means of a welding process.

As shown housing 2 comprises an annular shoulder 6 located a certain distance from the bottom of chamber 4. This shoulder serves to limit the depth to which the sensor is able to enter into chamber 4. The barrier layer is arranged a certain distance "above" this shoulder 6.

Figure 2:
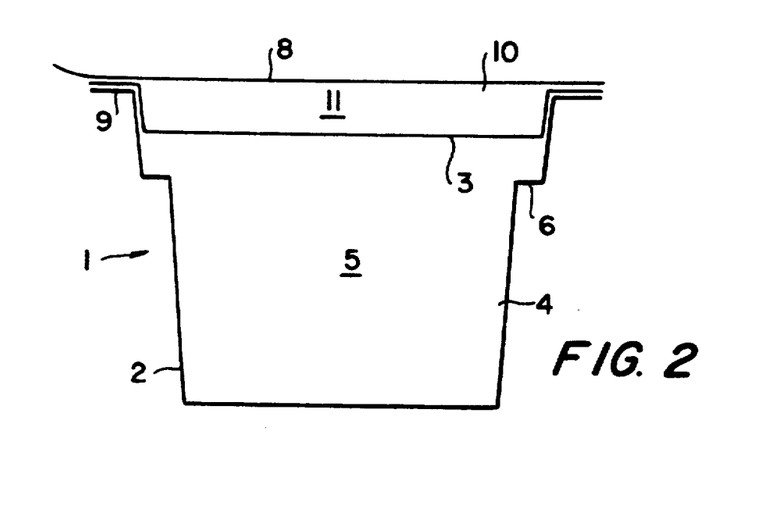

FIG. 2 depicts a calibration device identical to the one shown in FIG. 1, but supplemented with a lid 8 which is attached to an annular flange 9 extending along the rim of the housing. Lid 8 together with barrier layer 3 and housing 2 defines a second chamber 10. Said second chamber 10 is adapted to hold a second fluid 11 which in connection with the calibration process is to contact calibration fluid 5 in chamber 4. Lid 8 which normally will be made of the same material as the rest of the calibration device is preferably removably fastened to said device. Lid 8 may be either glued or welded to housing 2.

FIG. 2 further illustrates an advantageous form of barrier layer 3. Here, barrier layer 3 forms a sort of "pot-like" insert which is only fastened to housing 2 along flange 9, and the bottom of which extends in the predetermined distance from shoulder 6.

The embodiment illustrated in FIG. 2 is advantageous e.g. when a calibration is to be performed by means of a wet gas. In this case the calibration chamber contains a suitable wetting agent possibly in the form of an electrolyte, or in combination with an electrolyte.

For the sake of good order it is noted, that the wetting process in itself may effect a certain, minor shift in the concentration of the calibration fluid in the calibration chamber. It is, however, possible to compensate therefor simply by adjusting the basic concentration of the calibration fluid with a view to the desired concentration during calibration.

Figure 3:
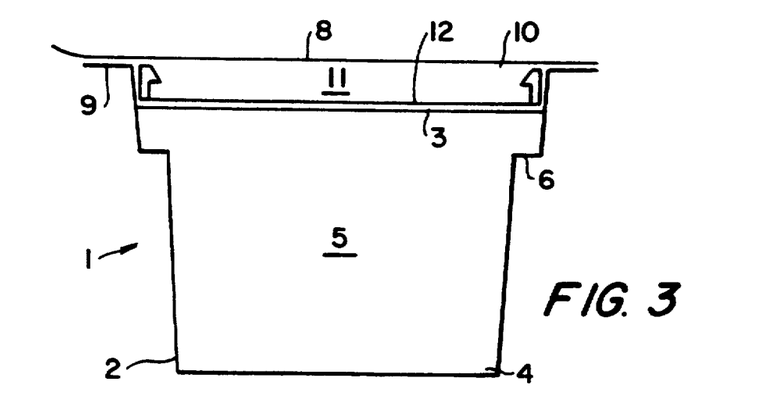

In FIG. 3 the calibration device is further supplemented with a membrane 12 accomodated in second chamber 10 between barrier layer 3 and lid 8.

The membrane is of a type known per se and consists of a thin, circular polymeric foil which along its outer edge is secured to a relatively rigid plastic ring having an annular, inwardly directed projection. The outer diameter of the plastic ring is slightly less than the inner diameter of second chamber 10, and the inner diameter of the ring is slightly larger than the diameter of calibration chamber 4. Due to the force subsequently exerted by the sensor the ring will engage shoulder 6 which thereby serves as a rest for the membrane ring during the fastening of said ring—and thus also the membrane—to the sensor.

Figure 4:
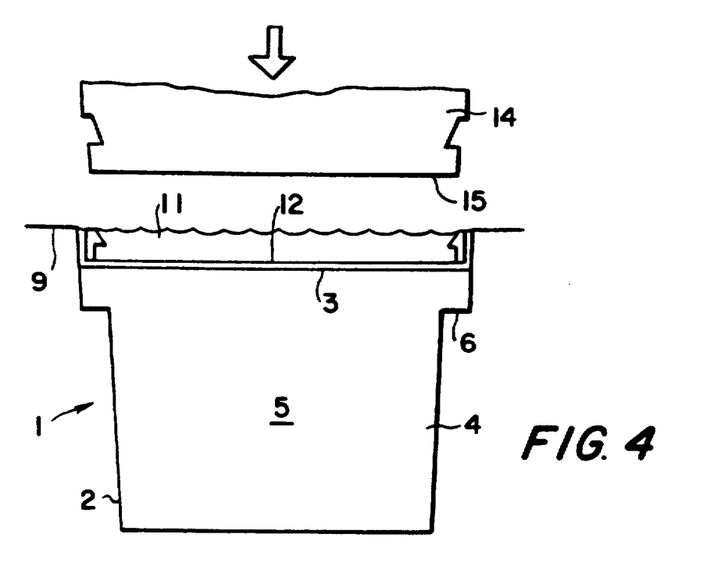

FIG. 4 depicts the calibration device at the beginning of a combined membrane replacement procedure and calibration process. The calibration device has been opened by removal of lid 8, and second chamber 10 is exposed with its content of wetting agent/electrolyte 11 and membrane 12. A sensor 14 with a measuring front surface 15 is ready to be inserted into the second chamber in the direction indicated by the arrow.

After a certain forward travel the sensor abuts the membrane ring and membrane 3 attached to this ring. If the sensor is advanced further in the direction of the arrow the side of the membrane ring facing the barrier layer will cause said layer to break. A point of importance in this context is, that the ruptured barrier layer must not contact (e.g. adhere to) the measuring surface of the sensor during the subsequent calibration process. In other words, the rupturing of the barrier layer must be effected in such a controlled or guided way that it is ensured that said layer does not impede or prevent free access between the membrane covered measuring surface of the sensor and the calibration fluid.

Such a guided rupturing might be attained by means of a suitable design of the side of the membrane ring facing the barrier layer. If, for example, the radially outer edge of the ring takes the form of a cutting edge along approx. $\frac{3}{4}$ of the circumference of the ring, and the remaining $\frac{1}{4}$ has a smooth rounded contour, approx. $\frac{3}{4}$ of the circumference of the barrier layer will be ruptured along the inner wall of the housing while the remaining $\frac{1}{4}$ will not be ruptured. Experiments have shown that this will cause the barrier layer to bend away in a more or less plane state, very similar to the lid of a tin.

Figure 5:
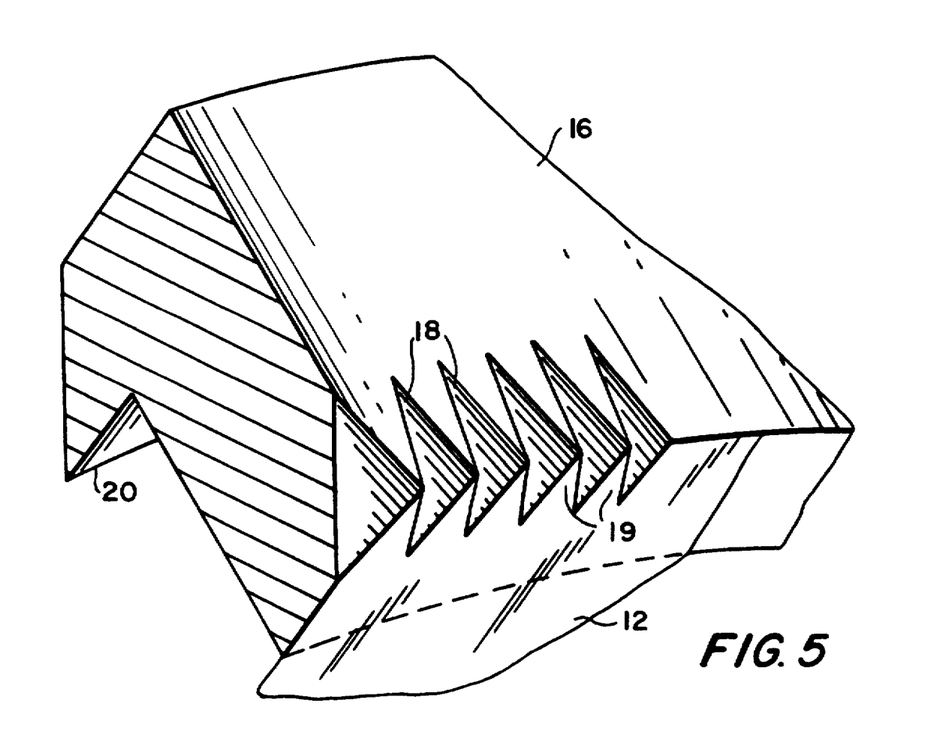

FIG. 5 shows a membrane ring which by simple means is provided with the above mentioned cutting properties. As shown, the ring has along its outer edge a relatively large number of closely spaced indentations 18, giving the ring a saw-like profile with points 19. These points effect the rupturing or cutting of the membrane layer along the desired portion of the circumference.

Alternatively the desired, guided rupturing of the barrier layer may be effected by a suitable arrangement of score lines or the like in the barrier layer proper.

Upon rupture of the barrier layer and after a certain travel the ring will abut shoulder 6 and as a result of further advancement of the sensor the ring will positively engage the sensor. The resulting outwardly directed deformation of the membrane ring will, due to the abutment against the inner side of housing 2, assist in providing the desired and necessary sealing between calibration chamber 4 and the surroundings.

Figures 6, 7, 8:
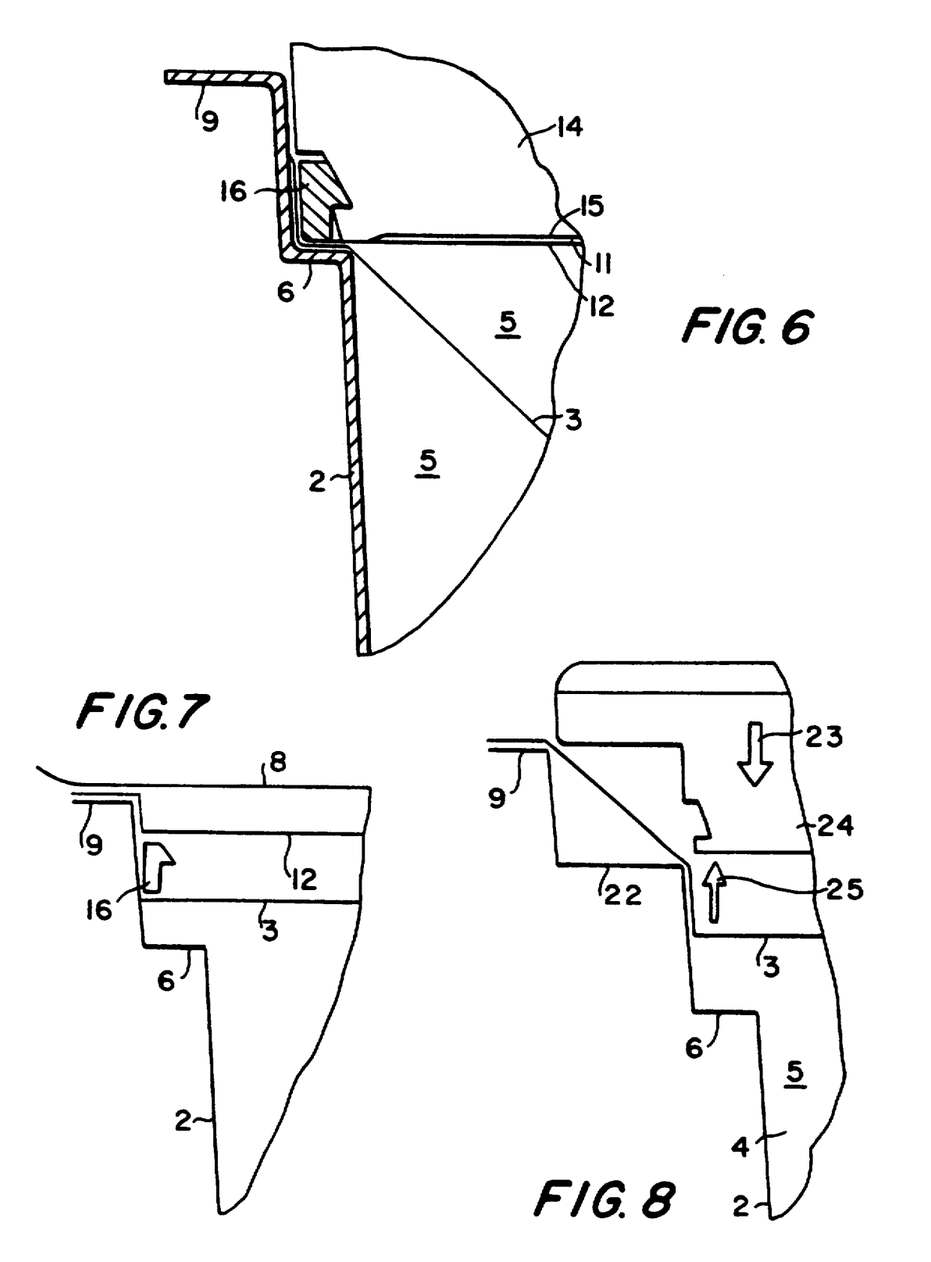

FIG. 6 illustrates, on a larger scale, a detail of the interconnection between the sensor and the calibration device during calibration. In the case shown the sensor consists in a sensor for transcutaneous registering of the $CO_2$-content in blood, a so-called Severinghaus-electrode. The working of said electrode depends on its pH-sensitive glass-section being electrically connected to the reference-section of the electrode via a suitable electrolyte, e.g. a bicarbonate solution. Accordingly the second fluid here consist of a bicarbonate solution, while the calibration fluid consists of a gas mixture with a suitable, predetermined content of $CO_2$, e.g. a mixture consisting of 5% $CO_2$, 20,9% $O_2$ and 74,1% $N_2$.

With a view to minimize the stabilization period of time of the sensor it is advantageous to use a bicarbonate solution having a content of $CO_2$ corresponding to a partial gas pressure value ($pCO_2$) in the range of e.g. 40-80 mmHg preferably about 60 mmHg. Since this value roughly corresponds to the $pCO_2$ value which the sensor will register during the subsequent transcutaneous measuring procedure the stabilization period of time of the sensor will be minimized. In the case of an $O_2$ sensor a suitable content of $O_2$ in the electrolyte in question would be of an order of magnitude corresponding to a partial gas pressure reading ($pO_2$) in the range of 40-170 mmHg.

As seen, membrane ring 16 engages sensor 14, so that membrane 12 is held in a stretched out state over measuring surface 15 of the sensor. Barrier layer 3 is ruptured and as previously explained bent away from the sensor and into the calibration chamber so that the calibration gas in the calibration chamber has free access to sensor 14. Some of the wetting liquid 11—in the form of an electrolyte liquid—which was originally held in second chamber 10 has, upon rupture of the barrier layer, contacted the calibration gas and effected the desired wetting of same. Some of liquid 11 is confined between measuring surface 15 of sensor 14 and membrane 12 as desired.

The radially outer side of sensor 14 and the back side or outer side of membrane ring 16, as mentioned, is pressed tight against the inner side of housing 2 which in connection with a film of electrolyte liquid also present here, entails that no fluid exchange between the surroundings and the calibration chamber can occur during calibration.

Even in case of a gaseous calibration fluid this sealing will normally be sufficient due to the fact that the pressure of the confined gas advantageously corresponds to the pressure of the surroundings.

This, however, does not exclude that in other cases it may be desirable or convenient to make use of supplementary sealing means between the sensor and the calibration device Such means could for example be a suitable, possibly separate O-ring.

In any circumstances it is to be ensured that the securing of the membrane ring to the sensor and said engagement between the outer side of the membrane ring and the inner side of the housing is mutually adapted in such a way that there is no risk of the membrane ring "sticking" in housing 2 when the sensor is removed from the calibration device upon completed calibration and/or membrane replacement.

As described above the interconnection between the sensor and the calibration device in this embodiment relies solely on the frictional engagement between the outer side of the sensor and the inner side of the housing of the calibration device.

To further ensure the mutual interconnection the housing and/or the sensor could be provided with various connection assisting means, such as projections, constrictions, spring locks etc. It is, however, also possible to envisage the necessary connection be effected by means of a purpose-built fixture either in the form of a separate tool or integral with the measuring equipment in question.

FIG. 7 shows an alternative embodiment of membrane 12 with its fixing ring. This embodiment differs from the above described one in that membrane ring 16 is not secured to the membrane proper, and in that said ring is located on the other side of the membrane, i.e. in between the membrane and barrier layer 3. Membrane ring 16 proper is not altered but could have any suitable cross-section, e.g. a circular cross-section. Membrane 12 is positioned in the housing by attachment to flange 9 of said housing. In case the sensor in question demands the presence of an electrolyte between its measuring surface and the membrane, the free membrane surface is offset a certain distance down into chamber 10 whereby an electrolyte reservoir is formed between the membrane and lid 8. If a wet calibration process is to be performed, said reservoir between the membrane and the barrier layer contains, as before, a suitable wetting agent, possibly the same electrolyte liquid.

In this connection it is noted, that, as regards calibration devices for wet gas calibrations and incorporating a membrane, it might be expedient during manufacture of said devices, to ensure the presence of a homogenously distributed layer of wetting liquid between the membrane and the barrier layer. This affords the best possible wetting conditions, i.a. due to the fact that the liquid then contacts the dry gas immediately upon breaking of the barrier layer.

In the embodiment shown in FIG. 8, housing 2 is provided with a supplementary shoulder 22 between the opening of housing 2 and shoulder 6. Shoulder 22 serves to increase the distance which the cutting edge of the membrane ring travels relative to barrier layer 3 during rupture of said layer. This is of importance in relation to the extent to which the partially cut off barrier layer "lid" will fold away from the measuring surface of the sensor. For the sake of clarity both the membrane ring and the membrane are omitted in FIG. 8.

The effect is obtained by arranging barrier layer 3 as shown in FIG. 8. As appears a part of layer 3—seen in cross section—forms a hypotenuse in a triangle the other two sides of which are formed by the shoulder 22 and the inner side of housing 2, respectively. When the sensor—as indicated by line 24—is inserted into the housing in the direction of arrow 23 the barrier layer will be forced in axial and radial directions towards the above-mentioned two sides of the triangle, this resulting in that the barrier layer being retracted in the direction of arrow 25. The attained effect is primarily important in connection with the use of a sensor whose forward directed measuring surface only projects insignificantly "above" the rest of the forward part of the sensor. Nothing prevents, however, this technique from being applied in connection with other embodiments of the calibration device.

One could also envisage the above described effect to be obtained in a different way, e.g. by increasing the axial length of the portion of the housing extending between shoulder 6 and the edge of the opening of the housing. This—together with a complementary formed, annular, axially directed recess in the sensor—gives the same effect.

To visualize the order of magnitude of the size of the calibration device the following dimensions of the calibration device as shown in FIG. 3 can be stated: The axial height ca. 10 mm, the diameter of calibration chamber 4 ca. 10 mm and the diameter of second chamber 10 ca. 12 mm. There is a distance of ca. 4 mm between shoulder 6 and the inner side of lid 8, and the distance between barrier layer 3 and shoulder is ca. 2 mm.

Figure 9:
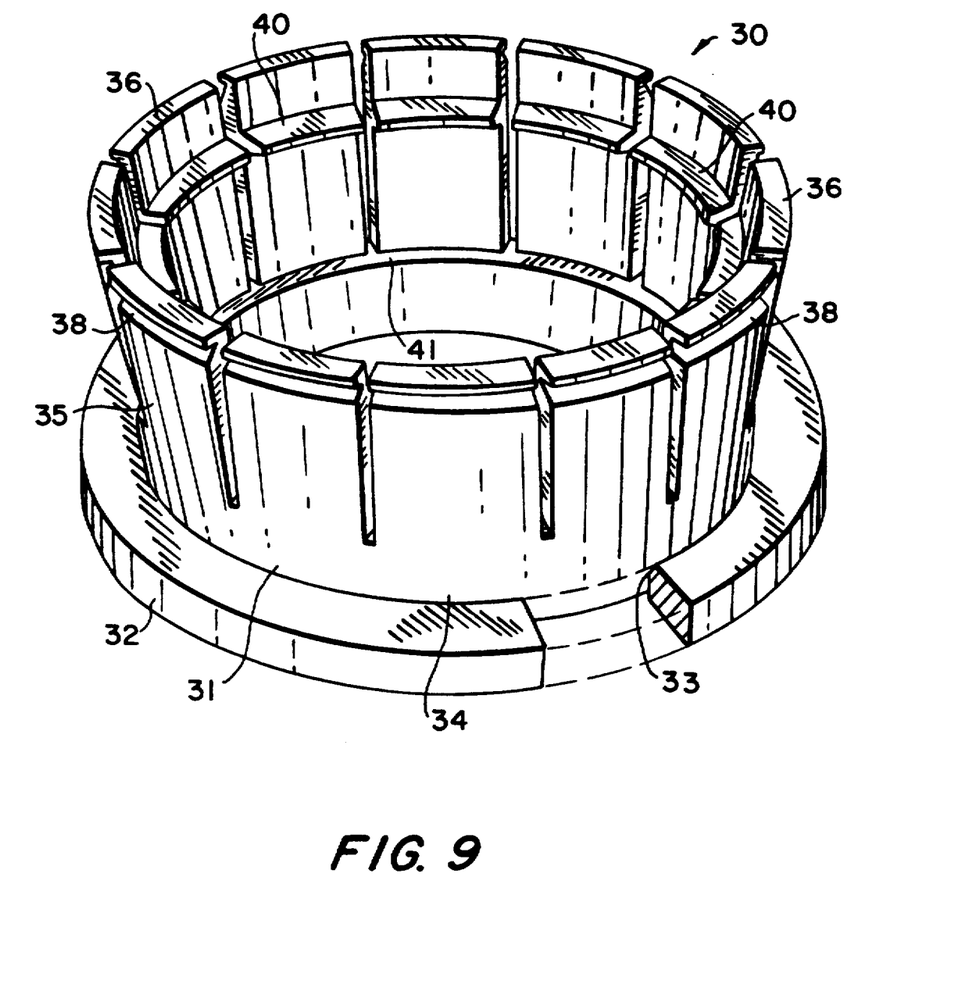

FIG. 9 shows a perspective view of an alternative embodiment of a membrane ring. The membrane ring 30—which in real life will have a somewhat larger d:h ratio than the one illustrated—is a two-piece construction consisting of a slotted squeezing ring 31 and a relatively rigid tightening ring 32 arranged about the squeezing ring. Both said rings are preferably made from a plastic e.g. POM (polyacetal). Tightening ring 32 has on its inner side facing the squeezing ring an annular projection 33 abutting the outer side of the squeezing ring. The tightening ring is slidable in the axial direction along the outer side of the squeezing ring, as will be explained in more detail later.

Squeezing ring 31 comprises a by and large circular cylindrical section 34 which smoothly passes into a conical, diverging section 35. As shown in the figure conical section 35 comprises a plurality of spring arms 36 arranged equidistantly along the circumference. Spring arms 36 branches off from cylindrical section 34, and due to this one-sided attachment they are able to move resiliently to and fro in the radial direction. When unbiased the arms take up the slightly outwardly sloping positions shown in FIG. 9.

Each spring arm 36 has on the outer side near its distal end a recess 38, and has on its inner side an inwardly directed projection 40. When spring arms 36 are forced radially inwards towards the center line of the squeezing ring, a by and large continuous, annular groove will be established on the outer side of the squeezing ring while on the inner side of said ring a by and large continuous, annular projection will be formed.

On the inner side of squeezing ring 31 there is an annular breast 41 at the bases of spring arms 36. The outwardly directed slopes of spring arms 36 are adjusted in such a way to the radial extension of projections 40 that an axis parallel projection of the innermost edge of said projections 40 approximately will coincide with the transition zone between breast 41 and spring arms 36.

Membrane ring 30 further comprises a membrane which is to be attached in a taut, stretched-out state across the measuring surface of the sensor concurrent with the fastening of the membrane ring to the sensor. This membrane—which is omitted in FIG. 9 for the sake of clarity, but appears in FIGS. 10 and 11—is initially fastened across the central aperture in the cylindrical end of the squeezing ring. This has been obtained by wrapping the membrane around the entire outer circumferential edge of the squeezing ring, the peripheral membrane part being held between said ring 31 and tightening ring 32.

Figure 10:
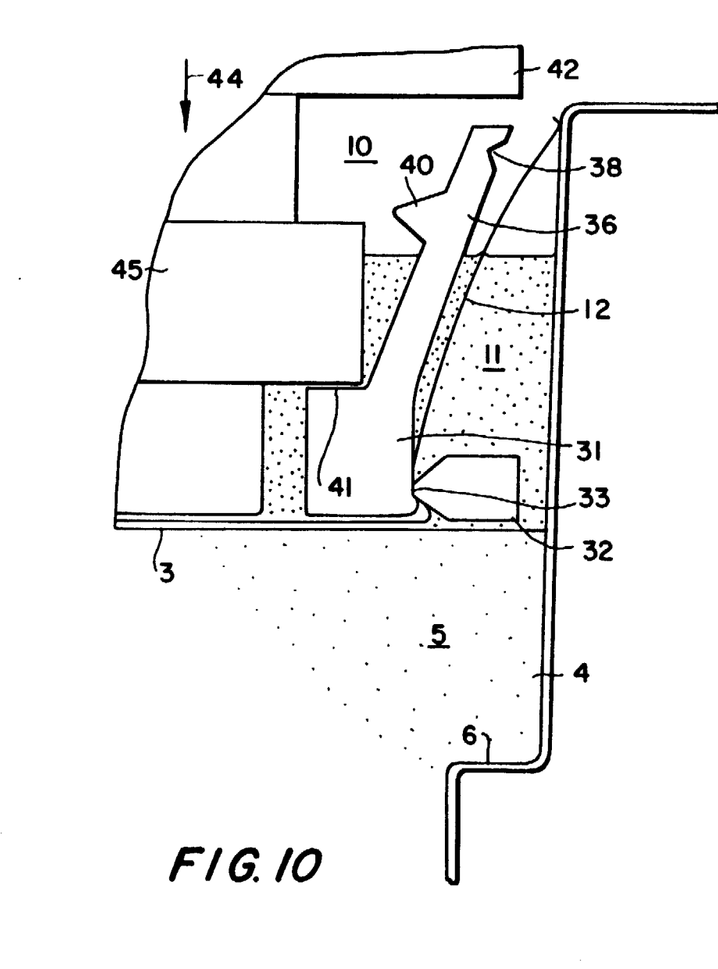
Figure 11:
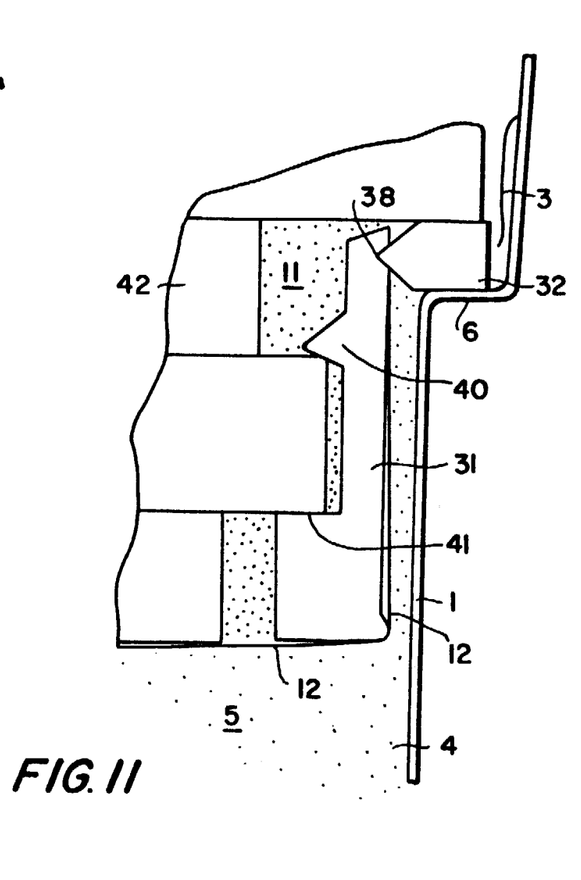

FIGS. 10 and 11 show schematically how the two-piece membrane ring 30 cooperates with the calibration device 1 and a sensor 42 during a combined calibration and membrane replacement procedure.

FIG. 10 depicts calibration device 1, membrane ring 30 and sensor 42 prior to a combined calibration and membrane replacement procedure. The lid of the calibration device has been removed, and sensor 42 has been partly inserted with its measuring surface ahead into the second chamber 10 by moving the sensor in the direction indicated by an arrow 44. As also shown, second chamber 10 contains a suitable amount of wetting agent/electrolyte 11. As previously mentioned membrane 12 proper is held between squeezing ring 31 and tightening ring 32.

In the situation shown sensor 42, which here possesses an annular shoulder 45, has been inserted into the calibration device to such an extent, that the front side of said shoulder just contacts breast 41 on squeezing ring 31. As appearing from FIG. 10 this insertion is possible because spring arms 36 in their unbiased rest positions are sloping outwards to the degree necessary to allow shoulder 45 to pass projections 40 on the separate spring arms. In the situation shown, barrier layer 3 has not yet been ruptured, and thus the calibration fluid in calibration chamber 4, e.g. a gas, is not in contact with the measuring surface of the sensor.

Upon further insertion of sensor 42 into the calibration device the situation appearing from FIG. 11 is reached. As shown in this figure barrier layer 3 has now been ruptured and membrane ring 30 has been attached to sensor 42 in such a way that membrane 12 is held in a taut, stretched-out state across the measuring surface of said sensor.

The fastening of the membrane ring to the sensor has been effected in the following way: After the under side of tightening ring 32 has ruptured barrier layer 3—in the guided manner previously described—tightening ring 32 abuts shoulder 6 of the calibration device. As a result of further downwards advancement of the sensor, tightening ring 32 has been displaced upwards along the outer side of the squeezing ring until engagement with groove(s) 38 near the distal ends of the spring arms. During this displacement of tightening ring 32 the spring arms have gradually been forced radially inwards with the result that their projections 40 have entered into engagement behind shoulder 45 on the sensor. The axial distance between projections 40 and breast 41 is adapted in such a manner to the axial height of shoulder 45 that membrane ring 30 be fastened axially indisplaceable to sensor 42. The engagement between tightening ring 32 and the locking groove 38 entails that the engagement between the membrane ring and the sensor is maintained after the calibration device has been removed from the sensor upon completed calibration. At the same time the relative displacement between tightening ring 32 and squeezing ring 31 has effected a tautening and stretching-out of membrane 12. Consequently, the system is now ready for calibration.

It is noted that in this state tightening ring 32 is held firmly between sensor 42 and shoulder 6. This entails partly that the sensor is prevented from being inserted further into the calibration device, partly that calibration chamber 4 is sealed against the surroundings during calibration. The mutual engagement between tightening ring 32 and sensor 42 will be maintained after separating the sensor and the calibration device, meaning that no unintended interaction can occur between the surroundings and the volume of electrolyte trapped between the sensor and the membrane. Upon completed calibration the sensor is separated from the calibration device and is now ready for use.

When, at a later time, it is desired to remove the membrane ring and the membrane from the sensor—e.g. in connection with a new calibration—this is done simply by displacing tightening ring 32 in the direction opposite the direction of the initial displacement, i.e. in the direction towards the cylindrical section 34 of squeezing ring 31. As the tightening ring approaches this section, spring arms 36 gradually return to their initial, slightly outwardly sloping rest positions meaning that projections 40 disengage breast 45 of sensor 42. Eventually membrane ring 30 as a whole will be released from the sensor which is then ready for a new calibration procedure etc.

We claim:

1. A process for calibrating a sensor in a calibration fluid, said process comprising:
   (a) holding a calibration fluid of a known composition or condition in a calibration chamber of a calibration housing, said calibration housing being adapted for engagement with said sensor for providing a releasable fluid-tight seal between said calibration housing and at least part of said sensor, said calibration chamber comprising a rupturable barrier on at least one side for enabling said calibration chamber to remain fluid-tight with said calibration fluid sealed therein prior to calibrating said sensor;
   (b) engaging said sensor with said calibration chamber at said rupturable barrier by applying said sensor against said barrier with sufficient force to rupture said barrier, thereby producing an opening in said barrier;
   (c) moving at least part of said sensor through said opening and into said calibration chamber so that at least part of said sensor contacts said calibration fluid therein, said sensor and said calibration housing engaging for providing a releasable fluid-tight seal of at least part of said sensor in said calibration chamber.

2. A process as defined in claim 1, wherein said calibration chamber of said calibration housing is a first fluid-tight chamber, said calibration housing further comprises a second fluid-tight chamber adjacent to said first fluid-tight calibration chamber containing a fluid having a second predetermined composition or condition, said second chamber being separated from said first chamber by said rupturable barrier, and being covered on at least one side by a lid for making said second chamber fluid-tight;
   and further comprising the steps of:
   (d) opening said lid of said second chamber;
   (e) inserting said sensor into and through said second chamber and rupturing said rupturable barrier for bringing said calibration fluid and said second fluid into mixing contact, said sensor and said calibration housing engaging for providing a releasable fluid-tight seal of at least part of said sensor in said calibration chamber.

3. A process as defined in claim 1 further comprising the steps of:
   (a) holding a calibration fluid of a known composition or condition in a fluid-tight calibration chamber of a calibration housing, said chamber comprising a rupturable barrier on at least one side;
   (b) applying the sensor against the barrier with sufficient force to rupture the barrier, thereby producing an opening in the barrier;
   (c) moving at least part of the sensor through the opening and into the chamber so that at least part of the sensor contacts the calibration fluid therein;
   (d) measuring the composition or the condition of the fluid with the sensor to obtain a corresponding measurement value; and
   (e) calibrating the sensor so that the measurement value is approximately equal to the known composition or condition of the fluid.

4. A process as defined in claim 3, wherein the calibrating step is performed while at least part of the sensor is in the chamber.

5. A device for calibrating a sensor, said device comprising;
   (a) a fluid-tight calibration chamber of a calibration housing, said chamber comprising a rupturable barrier on at least one side;
   (b) a calibration fluid inside the chamber, said fluid having a predetermined composition or condition, wherein said barrier is configured so that the sensor makes contact with the fluid when the barrier is ruptured by the sensor; and
   (c) a membrane configured essentially parallel to the barrier and outside of the first chamber, the membrane being permeable to components to which the sensor is sensitive, and the device further comprising a fixing means for cooperating with the membrane and the sensor to secure the membrane to the sensor in a stretched state when the sensor is essentially perpendicularly applied against the membrane.

6. A device as defined in claim 5, wherein the fixing means comprises an elastically deformable fixing ring secured to the side of the membrane facing away from the barrier layer, the fixing ring being configured to engage the sensor when the sensor is inserted into the fixing ring.

7. A device as defined in claim 5, wherein the fixing means comprises an elastically deformable fixing ring configured between the barrier and the membrane, the fixing ring being configured to engage the sensor when the sensor is inserted into the fixing ring.

8. A device as defined in claim 5, wherein the fixing means comprises a membrane ring comprising a tubular squeezing ring and a tightening ring, the latter being arranged radially about the former in such a way as to be axially displaceable along the outer side of the squeezing ring, the tightening ring being configured to maintain the membrane in a stretched state across the central aperture in the end of the squeezing ring facing the barrier, and the squeezing ring possessing a plurality of axially extending spring arms the distal ends of which are resiliently movable between a locking position and a rest position, wherein the spring arms are configured in slightly outwardly sloping positions as compared to the locking position, and the spring arms on their outer sides have locking means configured to engage with the tightening ring thereby locking the spring arms in the locking position, and the spring arms on their inner sides have engaging means which in the locking position of the arms are configured to engage with the sensor thereby attaching the membrane ring axially indisplaceable to the sensor.

9. A device as defined in claim 8, wherein the locking means on the spring arms are configured adjacent to the distal ends of the spring arms.

10. A device for calibrating in a calibration fluid, said device comprising a calibraton housing with at least two chambers, wherein
(a) a first fluid-tight chamber forms a calibration chamber holding a first fluid of a predetermined composition or condition, said first chamber having an opening sealed by a fluid-tight rupturable barrier;
(b) a second fluid-tight chamber is configured adjacent to said first fluid-tight chamber containing a second fluid of a predetermined composition or condition, said second chamber being separated from said first chamber by said rupturable barrier and being sealingly covered by a lid;
(c) said calibration housing is configured for engagement with said sensor for providing a releasable fluid-tight seal between at least part of said sensor and said first chamber when the sensor is inserted in said calibration housing through said second chamber and said barrier and into said first chamber.

11. A device as defined in claim 10, wherein barrier comprises a non-elastic material.

12. A device as defined in claim 10, wherein the first fluid comprises a dry gas with a known content of components to which the sensor is sensitive.

13. A device as defined in claim 12, wherein the dry gas is selected from the group consisting of $O_2$, $CO_2$, and combinations thereof.

14. A device as defined in claim 10, wherein the first and second chambers are configured so that the second fluid contacts the first fluid when the barrier is ruptured.

15. A device as defined in claim 14, wherein the first fluid is a dry gas and the second fluid is a liquid.

16. A device as defined in claim 15, wherein the second fluid contains bicarbonates.

17. A device as defined in claim 15, wherein the second fluid comprises a liquid containing a gas selected from the group consisting of:
(i) $CO_2$ in an amount corresponding to a partial gas pressure of carbon dioxide in the range of 40–80 mm Hg;
(ii) $O_2$ in an amount corresponding to a partial gas pressure in the range of 40–170 mm Hg; and
(iii) combinations of the foregoing.

18. A device that is suitable for use in the calibration of a sensor, said device comprising a sealed housing comprising at least two chambers, wherein
(a) a first fluid-tight calibration chamber is covered on at least one side by a fluid-tight, rupturable barrier, and said first chamber contains a first fluid having a predetermined composition or condition;
(b) a second chamber is configured adjacent to the first chamber and is separated from the first chamber by the fluid-tight, rupturable barrier, and said second chamber contains a second fluid and is covered on at least one side by a lid; and
(c) a membrane is configured essentially parallel to the barrier and outside of the first chamber, the membrane being permeable to components to which the sensor is sensitive, and the device further comprising a fixing means configured to cooperate with the membrane and the sensor in such a way that the membrane is secured to the sensor in a stretched state when the sensor is essentially perpendicularly applied against the membrane.

19. A device as defined in claim 18, wherein the fixing means comprises an elastically deformable fixing ring secured to the side of the membrane facing away from the barrier layer, the fixing ring being configured to engage the sensor when the sensor is inserted into the fixing ring.

20. A device as defined in claim 18, wherein the fixing means comprises an elastically deformable fixing ring configured between the barrier and the membrane, the fixing ring being configured to engage the sensor when the sensor is inserted into the fixing ring.

21. A device as defined in claim 18, wherein the fixing means comprises a membrane ring comprising a tubular squeezing ring and a tightening ring, the latter being arranged radially about the former in such a way as to be axially displaceable along the outer side of the squeezing ring, the tightening ring being configured to of maintain the membrane in a stretched state across the central aperture in the end of the squeezing ring facing the barrier, and the squeezing ring possessing a plurality of axially extending spring arms the distal ends of which are resiliently movable between a locking position and a rest position, wherein the spring arms are configured in slightly outwardly sloping positions as compared to the locking position, and the spring arms on their outer sides have locking means configured to engage with the tightening ring thereby locking the spring arms in the locking position, and the spring arms on their inner sides have engaging means which in the locking position of the arms are configured to engage with the sensor thereby attaching the membrane ring axially indisplaceable to the sensor.

22. A device as defined in claim 21, wherein the locking means on the spring arms are configured adjacent to the distal ends of the spring arms.

23. A device for calibrating a sensor in a calibration fluid, said device comprising a calibration housing with a calibration chamber holding a calibration fluid of a known composition or condition, wherein said calibration chamber has an opening for allowing said sensor to be at least partially inserted in said calibration chamber to enable said sensor to at least partially contact said calibration fluid during calibration of said sensor;

said opening is sealed by a fluid-tight rupturable barrier for enabling said calibration chamber to remain fluid-tight with said calibration fluid sealed therein prior to calibrating said sensor;

said barrier is rupturable by said sensor when at least part of said sensor is moved through said opening and into said calibration chamber and into contact with said calibration fluid; and said calibration housing is configured for engagement with said sensor for providing a releasable fluid-tight seal between at least part of said sensor and said calibration chamber when the sensor is inserted in said calibration housing.

24. A device as defined in claim 23 wherein said calibration housing comprises a rim extending around said opening, said rim cooperating with said sensor provide said releasable fluid-tight seal.

25. A device as defined in claim 23, wherein said device further comprises:

means for limiting the depth to which the sensor is capable of entering the housing.

26. A device as defined in claim 23, wherein the fluid comprises a dry gas with a known content of components to which the sensor is sensitive.

27. A device as defined in claim 26, wherein the dry gas is selected from the group consisting of $O_2$, $CO_2$, and combinations thereof.

28. A device as defined in claim 23, wherein the barrier of the calibration chamber comprises a non-elastic material.

29. A device as defined in claim 28, wherein the barrier comprises aluminum foil of a thickness of about 0.02–0.04 mm and the aluminum foil has a polymeric foil coating on at least one side.

* * * * *